(12) United States Patent
Wang et al.

(10) Patent No.: US 9,510,581 B2
(45) Date of Patent: Dec. 6, 2016

(54) BED BUG LURES

(71) Applicant: Rutgers, The State University of New Jersey, New Brunswick, NJ (US)

(72) Inventors: Changlu Wang, East Brunswick, NJ (US); Narinderpal Singh, East Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 41 days.

(21) Appl. No.: 14/357,425

(22) PCT Filed: Nov. 9, 2012

(86) PCT No.: PCT/US2012/064408
§ 371 (c)(1),
(2) Date: May 9, 2014

(87) PCT Pub. No.: WO2013/071075
PCT Pub. Date: May 16, 2013

(65) Prior Publication Data
US 2014/0311016 A1   Oct. 23, 2014

Related U.S. Application Data

(60) Provisional application No. 61/557,493, filed on Nov. 9, 2011.

(51) Int. Cl.
*A01M 1/02* (2006.01)
*A01N 65/22* (2009.01)
(Continued)

(52) U.S. Cl.
CPC .............. *A01M 1/023* (2013.01); *A01M 1/02* (2013.01); *A01M 1/103* (2013.01); *A01N 31/02* (2013.01); *A01N 35/02* (2013.01); *A01N 65/22* (2013.01)

(58) Field of Classification Search
CPC .............................. A01M 1/103; A01M 1/023
(Continued)

(56) References Cited

U.S. PATENT DOCUMENTS

| 2,675,293 A | * | 4/1954 | Baker | A01M 1/2077 43/129 |
| 4,263,740 A | * | 4/1981 | Hemsarth | A01M 1/02 43/114 |

(Continued)

OTHER PUBLICATIONS

Guerenstein et al., Host-seeking: how triatomines acquire and make use of information to find blood, Acta Tropica, 2009, pp. 148-158, vol. 110.

(Continued)

*Primary Examiner* — Marc Burgess
(74) *Attorney, Agent, or Firm* — Kathleen D. Rigaut; Dann, Dorfman, Herrell & Skillman (57) ABSTRACT

Various embodiments of the present invention provide a lure composition, lure arrangement, and/or method for attracting and capturing bed bugs and the like. In some embodiments, the present invention combines a collection structure with a chemical lure composition that has improved efficacy due to a synergistic combination of elements. The present invention reduces the need for sprayed or broadcast attractants. In one aspect of the invention, a lure composition for attracting bed bugs and the like is provided. The 5-chemical lure mixture comprises a combination of Nonanal, 1-octen-3-ol, L-lactic acid, spearmint oil, and coriander Egyptian oil. In another embodiment of the invention, the mixture comprises a 4-chemical lure mixture Nonanal, 1-octen-3-ol, spearmint oil, and coriander Egyptian oil.

7 Claims, 9 Drawing Sheets

(51) Int. Cl.
  *A01N 31/02* (2006.01)
  *A01N 35/02* (2006.01)
  *A01M 1/10* (2006.01)
(58) Field of Classification Search
  USPC .......................................................... 43/123
  See application file for complete search history.

(56) References Cited

U.S. PATENT DOCUMENTS

| | | | | |
|---|---|---|---|---|
| 6,286,249 | B1* | 9/2001 | Miller | A01M 1/02 43/113 |
| 2003/0061757 | A1* | 4/2003 | Askin | A01M 1/023 43/112 |
| 2003/0068295 | A1* | 4/2003 | Rohde | A61L 9/01 424/76.1 |
| 2003/0235601 | A1* | 12/2003 | Hallahan | A01N 43/16 424/405 |
| 2005/0220981 | A1* | 10/2005 | Renz | A23F 3/405 426/658 |
| 2007/0065394 | A1* | 3/2007 | Pinney | A61K 8/33 424/74 |
| 2010/0022469 | A1* | 1/2010 | Razzak | A01N 43/90 514/53 |
| 2011/0072711 | A1 | 3/2011 | Black et al. | |
| 2011/0072712 | A1* | 3/2011 | Black | A01M 1/02 43/123 |
| 2011/0203159 | A1 | 8/2011 | McKnight | |
| 2011/0229589 | A1 | 9/2011 | Elraz | |

OTHER PUBLICATIONS

Anderson et al., A carbon dioxide, heat and chemical lure trap for the bedbug, Cimex lectularius, Journal of Medical and Veterinary Entomology, 2009, pp. 99-105, vol. 23.

Wang et al., Bed bug (Heteroptera: Cimicidae) attraction to pitfall traps baited with carbon dioxide, heat, and chemical lure, Journal of Economic Entomology, 2009, pp. 1580-1585, vol. 102.

Wertheim et al., Pheromone-mediated aggregation in nonsocial arthropods: an evolutionary ecological perspective, Annual Review of Entomology, 2005, pp. 321-346, vol. 50.

Siljander et al., Evidence for male- and juvenile-specific contact pheromones of the common bed bug Cimex lectulari us, Entomologia Experimentalis et Applicata, 2007, pp. 215-219, vol. 125.

Boase et al., Bedbugs-back from the brink, Pesticide Outlook, 2001, pp. 159-162, vol. 12.

Guerenstein et al., Olfactory and behavioural responses of the blood-sucking bug *Triatoma infestans* to odours of vertebrate hosts, The Journal of Experimental Biology, 2001, pp. 585-597, vol. 204.

Ghaninia et al., Natural odor ligands for olfactory receptor neurons of the female mosquito *Aedes aegypti*: Use of gas chromatography linked single sensillum recordings, The Journal of Experimental Biology, 2008, pp. 3020-3027, vol. 211.

Meijerink et al., Olfactory receptors on the antennae of the malaria mosquito *Anopheles gambiae* are sensitive to ammonia and other sweat borne components, Journal of Insect Physiology, 2001, pp. 455-464, vol. 47.

Syed et al., Acute olfactory response of Culex mosquitoes to a human- and bird-derived attractant, Proceedings of the National Academy of Sciences of the United States of America, 2009, pp. 18803-18808, vol. 106.

Barrozo et al., Orientation response of haematophagous bugs to $CO_2$, the effect of the temporal structure of the stimulus, Journal of Comparative Physiology A: Neuroethology, Sensory, Neural, and Behavioral Physiology, 2006, pp. 827-831, vol. 192.

Maranga et al., Attraction of *Amblyomma variegatum* (ticks) to the attraction-aggregation-attachment pheromone with or without carbon dioxide, Experimental and Applied Acarology, 2003, pp. 121-130, vol. 29.

Rueda et al., Evaluation of 1-octen-3-ol,carbon dioxide, and light as attractants for mosquitoes associated with two distinct habitats in North Carolina, Journal of the American Mosquito Control Association, 2001, pp. 61-66, vol. 17.

Wang et al., Effectiveness of bed bug monitors for detecting and trapping bed bugs in apartments, Journal of Economic Entomology, 2011, pp. 274-278, vol. 104.

* cited by examiner

BED BUG LURES

This application is a §371 national phase entry of PCT/US2012/064408 filed Nov. 9, 2012, which claims priority to U.S. Provisional Application 61/557,493 filed Nov. 9, 2012, the entire contents being incorporated herein by reference as though set forth in full.

Pursuant to 35 U.S.C. §202(c) it is acknowledged that the U.S. Government has rights in the invention described herein, which was made in part with funds from the US Department of Housing and Urban Development, Grant Number NJLHH0197-09.

FIELD OF THE INVENTION

This invention relates to the fields of insect trapping and eradication. More specifically, the invention provides an improved insect attractant formulation for treating bedbug infestations.

BACKGROUND OF THE INVENTION

Several publications and patent documents are cited throughout this application in order to more fully describe the state of the art to which this invention pertains. The disclosure of each of these citations is incorporated by reference herein.

Hematophagous insects use a variety of visual, mechanical, chemical, and thermal cues to detect vertebrate hosts [1]. Host searching behavior in unfed bont tick, *Amblyomma hebraeum* Koch [2, 3], and *Glossina* spp. (Diptera: Glossinidae) [4] is stimulated by carbon dioxide ($CO_2$) emitted by mammalian hosts. Odors from human skin [5], sweat, breath and body odors from cattle, birds, and mice [6], bird feathers or skin [7], and bird uropygial glands [8], play a major role in attracting different families of hematophagous mosquitoes. Bed bugs (*Cimex lectularius* L.) have been found to be attracted to $CO_2$ [9, 10, 11], heat and chemical odors [10, 11, 12, 13]. Anderson [10] demonstrated the effectiveness of a trap baited with $CO_2$ (50-400 ml/min), heat (37.2-42.2° C.) and a chemical lure comprised of 33.0 µg propionic acid, 0.33 µg butyric acid, 0.33 µg valeric acid, 100 µg 1-octen-3-ol (octenol) and 100 µg L-lactic acid. In a separate study, Wang [11] confirmed the effectiveness of $CO_2$ (169 ml/min) and heat (43.3-48.8° C.) in their attraction to bed bugs. However, none of these studies confirmed the effectiveness of chemical lures alone or interactions among chemical lures, heat, and $CO_2$.

Over 300 nonsocial arthropod species belonging to 51 families in 12 different orders were reported to use aggregation pheromones [14]. Bed bug nymphs showed specific preference for paper discs that had been exposed to conspecifics of the same developmental stage [15]. Siljander [16] identified air borne aggregation pheromones that consisted of many chemical components including, (E)-2-hexenal, (E)-2-octenal, (2E, 4E)-octadienal, benzaldehyde, nonanal, decanal, sulcatone, (+)-limonene, (−)-limonene, and benzyl alcohol. These chemicals were attractive to nymphs in olfactometer bioassays. These pheromones could potentially be used for monitoring bed bugs; however their effectiveness has not been tested yet in arenas under conditions that simulate field conditions.

Bed bugs hide during the day and are difficult to locate as they are small and elusive. Therefore, developing effective monitoring tools has been recognized as a critical component in the current campaign for fighting bed bug resurgence [17]. Most of the available monitors incorporate one or several non-chemical and chemical lures to attract and capture hungry bed bugs foraging for blood meals. However, the data on the role of various lures in the effectiveness of monitors are very limited.

SUMMARY OF THE INVENTION

Various embodiments of the present invention provide a lure composition, lure arrangement, and/or method for attracting and capturing bed bugs and the like. In some embodiments, the present invention combines a collection structure with a chemical lure composition that has improved efficacy due to a synergistic combination of elements. The present invention reduces the need for sprayed or broadcast attractants.

In one aspect of the invention, a lure composition for attracting bed bugs and the like is provided. The 5-chemical lure mixture comprises a combination of Nonanal, 1-octen-3-ol, L-lactic acid, spearmint oil, and coriander Egyptian oil. In another embodiment of the invention, the mixture comprises a 4-chemical lure mixture Nonanal, 1-octen-3-ol, spearmint oil, and coriander Egyptian oil.

In another embodiment of the invention, a lure arrangement for attracting bed bugs and the like is provided. The lure arrangement comprises a heat source, a carbon dioxide source, and a lure mixture. The lure mixture comprises a combination of Nonanal, 1-octen-3-ol, L-lactic acid, spearmint oil, and coriander Egyptian oil.

In another aspect of the invention, a lured trap is provided. The trap includes a climb-up pitfall structure in which a lure mixture is disposed. The trap may also include a heat source, and a carbon dioxide source, which together with the lure mixture form a lure arrangement associated with the trap.

Another embodiment of the invention facilitates trapping of bed bugs by providing a lure mixture within a climb-up pitfall trap, and positioning the lured trap in an infested environment. The lured trap may further be provided with a lure arrangement, which may be activated to produce gaseous vapors enhancing the effect of the lure mixture. Such traps may also include an insecticide effective for killing bed bugs.

Finally, the lure of the invention may be incorporated into a bed bug monitor in order to assess the effectiveness of bed bug eradication procedures.

BRIEF DESCRIPTION OF THE DRAWINGS

FIG. 10: Experimental setup for determining bed bug attraction to chemical lures in plastic tray arenas.

DETAILED DESCRIPTION OF THE INVENTION

Commercial bed bug monitors incorporating heat, carbon dioxide ($CO_2$) and chemical lures are being used for detecting bed bugs; however, there are few reported studies on the effectiveness of chemical lures in bed bug monitors and the interactions among chemical lure, $CO_2$, and heat. We screened 12 chemicals for their attraction to bed bugs and evaluated interactions among chemical lures, $CO_2$, and heat. The chemical lure mixture consisting of nonanal, 1-octen-3-ol, spearmint oil, and coriander Egyptian oil was found being most attractive to bed bugs and significantly increased the trap catches in laboratory assays. Adding this chemical lure mixture when $CO_2$ was present increased the trap catch by 1.6-fold compared with traps baited with $CO_2$ alone. Whereas, adding heat did not significantly increase trap catches when $CO_2$ was present. Results suggest a combination of chemical lure and $CO_2$ is essential for designing effective bed bug monitors.

The following materials and methods are provided to facilitate the practice of the present invention.

Insects

Bed bugs were collected from an infested house in Lakewood, N.J. They were maintained in plastic containers (4.7 cm height and 5 cm diameter) with folded paper as harborages at 26° C.±1° C., 40±10% relative humidity, a 12:12 hour (L:D) photoperiod, and were deprived of food for the entire duration of the study. All bioassays were conducted within 3 months after bed bugs were collected.

Pitfall Trap and Experimental Arenas

Figure 1A:
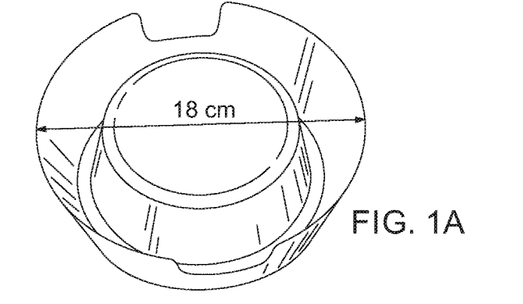
FIG. 1: Experimental set up for determining bed bug attraction to non-chemical and chemical lures: a) pitfall trap used in all bioassays; b) a plastic tray arena with a baited and an unbaited control trap; c) a wooden door arena with a trap baited with $CO_2$, heat and chemical lure, and an unbaited control trap.

Pitfall traps were used to evaluate the attractiveness of lures. The pitfall trap was an inverted plastic dog bowl (600 ml volume, 18 cm diameter, 6.4 cm deep and 1 mm thickness) (IKEA, Baltimore, Md., USA) (FIG. 1a). The outer wall of the trap was covered with a layer of paper surgical tape (Caring International, Mundelein, Ill., USA), which was painted black with ColorPlace spray paint (WalMart Stores Inc., Bentonville, USA). Bed bugs preferred black color to white color in our preliminary bioassays.

Figure 1B:
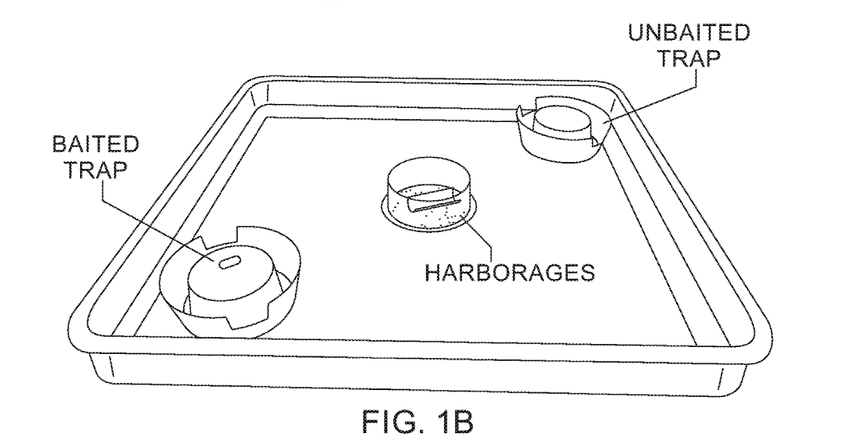

Two types of experimental arenas were used: a) wooden door arenas (200 by 76 cm by 6.4 cm) (length by width by height) with wooden floor, and b) plastic tray arenas (80 by 75 by 5 cm) (length by width by height) with bottom lined with brown paper (FIG. 1b). A layer of fluoropolymer resin (DuPont Polymers, Wilmington, Del., USA) was applied to inner walls of the experimental arenas to prevent the bugs from escaping. A layer of this resin was also applied to inner walls of the pitfall traps in a similar fashion to confine the bed bugs that fell into the traps. A filter paper (15 cm diameter) was placed on the floor in the center of each arena, and then a plastic ring (13.3 cm diameter and 6.4 cm height) was placed on the filter paper for confining the bed bugs. A piece of folded cardboard and folded fabric was placed on the filter paper to provide harborages for bed bugs. Six additional paper harborages measuring 5.1 cm long and 3.3 cm wide were placed along the edges of the floor of each wooden arena. Two wooden door arenas were located at least 6 m away from each other in a 15 m long and 9 m wide room at 23-25° C. Two additional wooden door arenas were located in two 4 m long and 2.3 m wide rooms at 24-25° C. These rooms had normal air current through vents on the ceilings or through the open door. In experiments using plastic tray arenas, four arenas were placed simultaneously in a non-ventilated, closed room measuring 4 m long and 2.3 m wide at 24-25° C. A 12:12 hour (L:D) cycle was maintained in all the rooms that were used for bioassays.

Effect of $CO_2$ Release Rates on Bed Bug Trap Efficacy

Figure 1C:
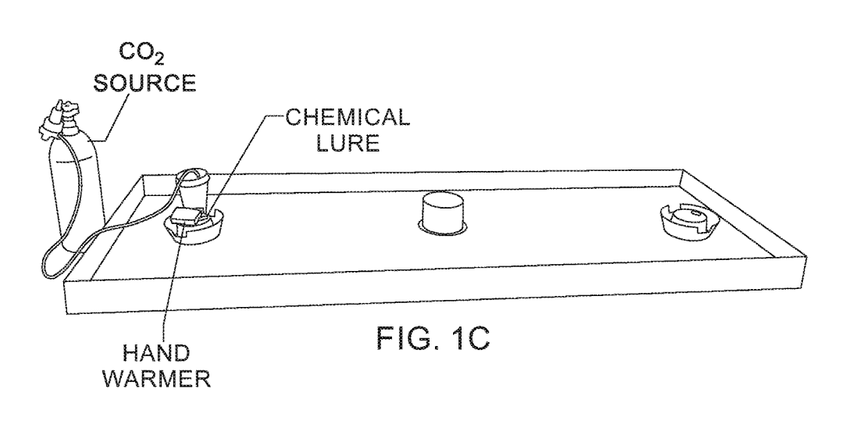

Four door arenas were used and each arena had an unbaited control pitfall trap and a pitfall trap baited with $CO_2$. The two traps were placed at opposite ends equidistant (85 cm) from the center. The experiment was tested over 4 consecutive days. On each day, a different $CO_2$ release rate was used in each arena following a Latin square design. The $CO_2$ source was 5 lb cylinders (Airgas East Inc., Piscataway, N.J., USA). The tested release rates were: 200, 300, 400 and 500 ml/min. The rate was determined as ml of water displaced by $CO_2$ per unit of time using a Bubble-O-Meter (Bubble-O-Meter, Dublin, Ohio, USA). The $CO_2$ was introduced into 240 ml plastic cups that were placed on the pitfall traps (FIG. 1c). Two holes were made on the lid of each plastic cup for $CO_2$ to escape. Fifty bed bug nymphs and adult males were released into the center of each arena and confined with a plastic ring. The bugs were acclimated for approximately 15 hours before starting the treatments. At 1 hour after dark cycle, the plastic ring confining the bugs was removed. The numbers of bed bugs trapped in the pitfall traps and those in the arenas were collected and counted after 8 hours. An 8 hour period has been observed to be sufficient for observing the effect of lures on bed bug behavior in preliminary bioassays. The number of dead or moribund bed bugs in each arena was very low (<5%) in all the bioassays. After counting, dead and moribund bugs were replaced with healthy bugs in each arena. All bugs were placed back to the center of the arenas and confined with plastic rings for 15 hours before starting next bioassay.

Effect of Heat on Bed Bug Trap Efficacy

This experiment was conducted in four plastic tray arenas. Mini hand warmers were used as the heat source (Grabber, Grand Rapids, Mich., USA). Two pitfall traps were placed at opposite corners of each arena equidistant (25 cm) from the center. One trap received either two or four mini hand warmers, and the other trap was used as an unbaited control. The surface temperature of the hand warmer was 40-48° C. during the first 6 hours. The air temperatures on the floor of arenas 1 cm away from the pitfall trap baited with 2 and 4 hand warmers were: 0.2-0.3° C. and 0.5-0.6° C., above the ambient temperature, respectively. The air temperatures at the lip of pitfall trap baited with 2 and 4 hand warmers were: 0.8-0.9° C. and 1.3-1.6° C., above the ambient temperature, respectively. These temperatures were based on hourly recordings of one monitor during the first 6 hours after trap placement using a thermocouple thermometer (Cole-Parmer Instrument Company, Vernon Hills, Ill., USA). Each treatment was replicated 6 times over 3 consecutive days. Fifty bed bugs were released into each arena and the testing procedure was same as in Experiment 2.3.

Effect of Heat on Bed Bug Trap Efficacy when $CO_2$ is Present $CO_2$ at 200 ml/min was selected based on results from Experiment 2.3. This rate is similar to the respiration rate of an adult human at rest (250 ml/min) [18]. $CO_2$ alone or in combination with 2, 3 or 4 mini hand warmers were tested in four wooden door arenas on the same day under similar conditions as in Experiment 2.3. Each treatment was assigned to a different arena and the experiment was repeated four times over four consecutive days following a Latin square design. Each arena had an unbaited control trap and a baited pitfall trap placed on opposite ends of the test arena. Fifty bed bugs were released into each arena and the testing procedure was same as described above.

Screening of Chemical Lures for Attraction to Bed Bugs in Four-Choice Bioassays

Twelve known or potential bed bug chemical lures (Table 1) were evaluated for their attractiveness to bed bugs in plastic tray arenas. The chemicals were randomly divided into 4 groups. Each group was tested in the same arenas to evaluate the attractiveness of the chemicals. A 50 µl of each chemical was dispensed on cotton within a 0.7 ml micro centrifuge tube. The lid of each tube had a 2 mm diameter opening to allow for slow release of the chemical. Four arenas were used and in each arena, four pitfall traps were placed at four corners equidistant (25 cm) from the center. Three traps in each arena were baited with three different chemical lures that fallen into the same group as listed in Table 1 and the fourth trap was an unbaited control. Each group of chemical lures was tested 8 times over two consecutive days. Fifty bed bugs were released into each arena and the testing procedure was the same as described above.

were placed at opposite corners of each arena (FIG. 1b). One trap was used as an unbaited control and the other trap received a chemical lure. Each chemical lure was evaluated 8 times over two consecutive days. The baited and non-baited trap positions in each arena were switched on the second day to eliminate any positional effect that could influence the trap catch.

Relative Attractiveness of Chemical Lures to Bed Bugs in Four-Choice Bioassays

The relative attractiveness of four most effective chemicals: nonanal, 1-octen-3-ol, spearmint oil and coriander Egyptian oil identified from earlier experiments evaluated using the same method as described above. Four traps in each arena were baited with one of these chemicals. Four arenas were used to obtain four replicates.

Attractiveness of a Chemical Lure Mixture to Bed Bugs.

Nonanal, 1-octen-3-ol, spearmint oil and coriander Egyptian oil were confirmed as exhibiting a significant attraction to bed bugs. We examined the attractiveness of a mixture of these four chemical lures. Ten microliter of each chemical was dispensed onto cotton within a 0.7 ml micro centrifuge tube. Four tray arenas were used and in each arena, one trap was used as an unbaited control and the other trap received a chemical lure mixture (40 µl) (FIG. 1b). The experiment was repeated the next day. The baited and non-baited trap positions in each arena were switched on the second day. Other procedures were the same as described above.

The attractiveness of the four-chemical lure mixture was also compared with each individual lure component. A 40 µl of individual chemical lure was dispensed on cotton within a 0.7 ml micro centrifuge tube. Four tray arenas were used and in each arena, two traps were placed at opposite corners. One trap received one of the four chemicals and the other trap received a four-chemical lure mixture. On each day, a different chemical was tested in each arena. The experiment

TABLE 1

Percent catch of bed bugs in pitfall traps baited with three chemical lures and an baited control

| Group | Chemical Lure | N | Mean (%) ± SE | $\chi^2$ | P-value | Source of material |
|---|---|---|---|---|---|---|
| I | 1-octen-3-ol | 8 | 28.3 ± 2.5a$^a$ | 13.2 | 0.004 | Bedoukian Research Inc. |
| | L-lactic acid | 8 | 25.7 ± 2.7a | | | Bedoukian Research Inc. |
| | Coriander Egyptian oil | 8 | 24.2 ± 4.8a | | | New Directions Aromatic |
| | Control | 8 | 12.0 ± 1.3b | | | |
| II | L-carvone | 8 | 27.5 ± 3.5a | 13.6 | 0.003 | Bedoukian Research Inc. |
| | Spearmint Oil | 8 | 25.0 ± 2.2ab | | | Bedoukian Research Inc. |
| | Styralol | 8 | 16.4 ± 2.4bc | | | Bedoukian Research Inc. |
| | Control | 8 | 14.6 ± 1.1c | | | |
| III | Nonanal | 8 | 27.7 ± 3.2a | 10.1 | 0.01 | Sigma-Aldrich Co. |
| | Benzyl alcohol | 8 | 25.1 ± 3.4ab | | | Sigma-Aldrich Co. |
| | 6-Methyl-5-Hepten-2-one | 8 | 20.9 ± 2.52ab | | | Sigma-Aldrich Co. |
| | Control | 8 | 15.1 ± 1.8b | | | |
| IV | Insect Biting Lure | 4 | 21.5 ± 3.5 a | 3.0 | 0.4 | Bedoukian Research Inc. |
| | R-octenol + $NH_3HCO_3$ | 4 | 18.3 ± 6.3a | | | Bedoukian Research Inc. |
| | Z-Geranyl Acetone | 4 | 13.0 ± 2.4a | | | Bedoukian Research Inc. |
| | Control | 4 | 12.0 ± 3.7a | | | |

Attractiveness of Chemical Lures to Bed Bugs in Two-Choice Bioassays

Nonanal, 1-octen-3-ol, spearmint oil, coriander Egyptian oil, L-lactic acid, and L-carvone exhibited significant attraction to bed bugs. These chemicals were further evaluated to confirm their attractiveness to bed bugs using two-choice assays. The experimental setup and testing procedure were similar to those described above however only two traps was repeated four times over four consecutive days following a Latin square design. Other procedures were same as described above.

Attractiveness of a Chemical Lure Mixture when $CO_2$ and Heat were Present: Comparison Between $CO_2$ Alone and $CO_2$+Chemical Lure+Heat Two door arenas were baited with $CO_2$ (200 ml/min) and two arenas were baited with combination of $CO_2$ (200 ml/min), heat (4 mini hand warmers), and a chemical lure mixture as discussed above (FIG. 1c). The experiment was repeated four times over four consecutive days to obtain 8 replicates. The baited and non-baited trap positions in each arena were switched after two days.

Comparison Between $CO_2$ Alone and $CO_2$+Chemical Lure

Two door arenas were baited with $CO_2$ (200 ml/min) and two arenas were baited with combination of $CO_2$ (200 ml/min) and the chemical lure mixture. The experiment was repeated three times over three consecutive days to obtain 6 replicates. The baited and non-baited trap positions in each arena were switched on the third day. The experimental procedures were same as described above.

Statistical Analyses

Percent attraction in multiple comparison experiments involving a control was calculated as: Percent attraction=100×(T−C)/Total, where "T" is the number of bed bugs in the baited pitfall trap and "C" is the number of bed bugs in the non-baited pitfall trap. "Total" is the total number of healthy bugs in each experiment arena at time of recording the bed bug locations. The percent catch is the number of bed bugs found in a pitfall trap divided by number of healthy bed bugs in each arena at the time of recording the results. Positive values indicate attraction to the treatment and negative values indicate repellency; and the values range from −100 (complete repellency) to +100 (complete attraction) [19]. For the paired design experiments, mean percent catch were analyzed by paired t-test (P=0.05). Mean percent attractions among the treatments were compared using the non-parametric Kruskal-Wallis tests followed by Tukey's HSD test. The data for Experiment 2.10.1 and 2.10.2 were pooled for analyzing differences among treatments (treatment×day interaction was insignificant from Analysis of Variance test) [20].

The following example is provided to illustrate certain embodiments of the invention. It is not intended to limit the invention in any way.

EXAMPLE I

Figure 2:
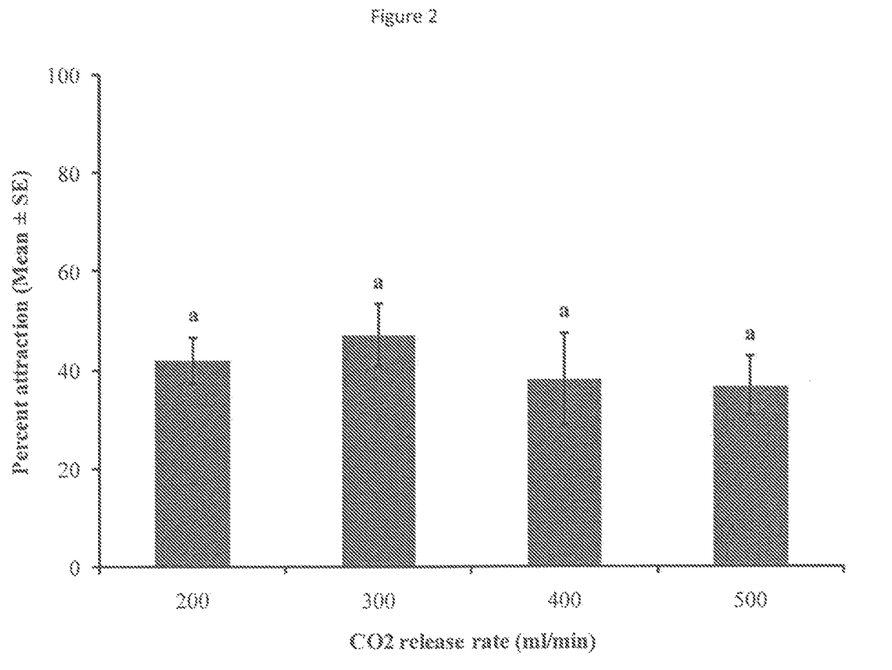
FIG. 2: Attraction of bed bugs to pitfall traps baited with $CO_2$. Bars with same letters are not significantly different ($P>0.05$, Tukey's HSD test).
Figure 3:
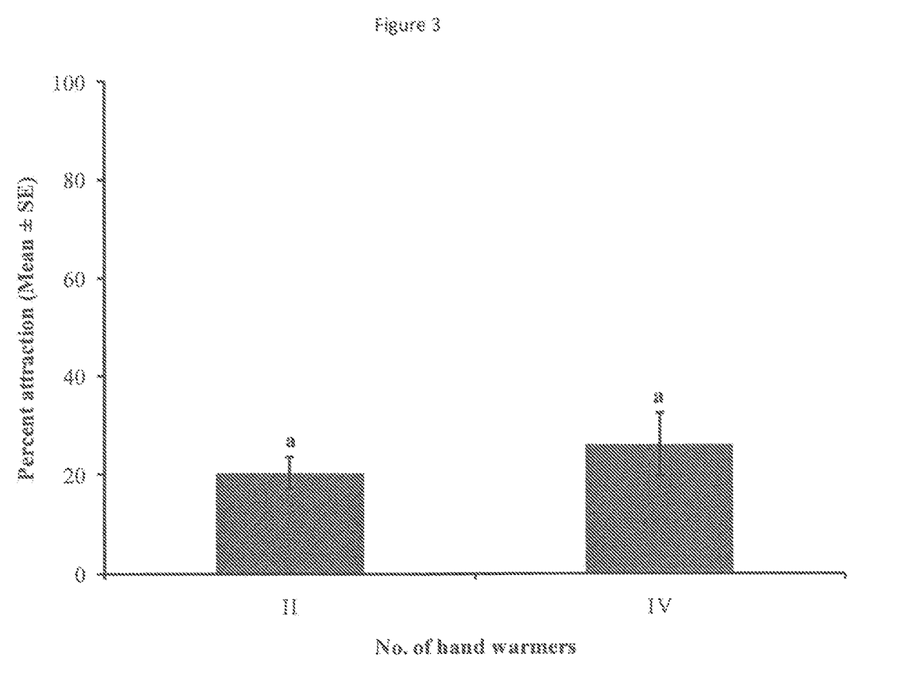
FIG. 3: Attraction of bed bugs to pitfall traps baited with heat (either two or four mini hand warmers). Bars with same letters are not significantly different ($P>0.05$, Tukey's HSD test).
Figure 4:
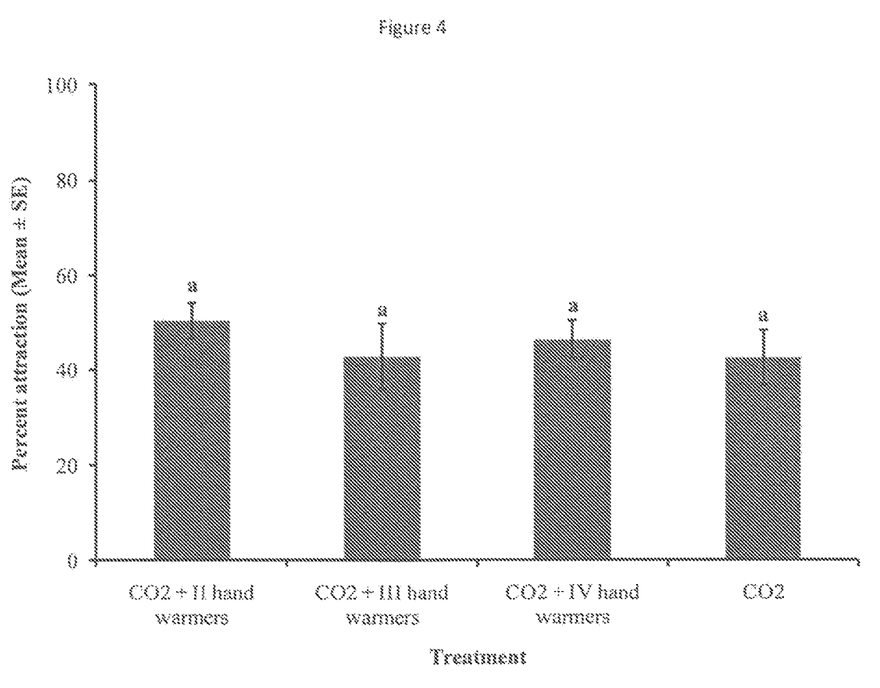
FIG. 4: Attraction of bed bugs to pitfall traps baited with $CO_2$ (200 ml/min) alone or in combination with heat (two, three or four mini hand warmers). Bars with same letters are not significantly different ($P>0.05$, Tukey's HSD test).

The $CO_2$ release rates were not significantly different in their attraction to bed bugs ($\chi^2$=2.30, df=3, P=0.52, Kruskal-Wallis Tests) (FIG. 2). Heat (two or four mini hand warmers) significantly increased trap catches (P<0.05) although there were no significantly differences between the two heat sources ($\chi^2$=0.32, df=1, P=0.58, Kruskal-Wallis Tests) (FIG. 3). There were no significant differences among pitfall traps baited with $CO_2$ alone or in combination with 2, 3 or 4 hand warmers in door arenas (FIG. 4) ($\chi^2$=0.97, df=3, P=0.86, Kruskal-Wallis Tests).

Figure 5:
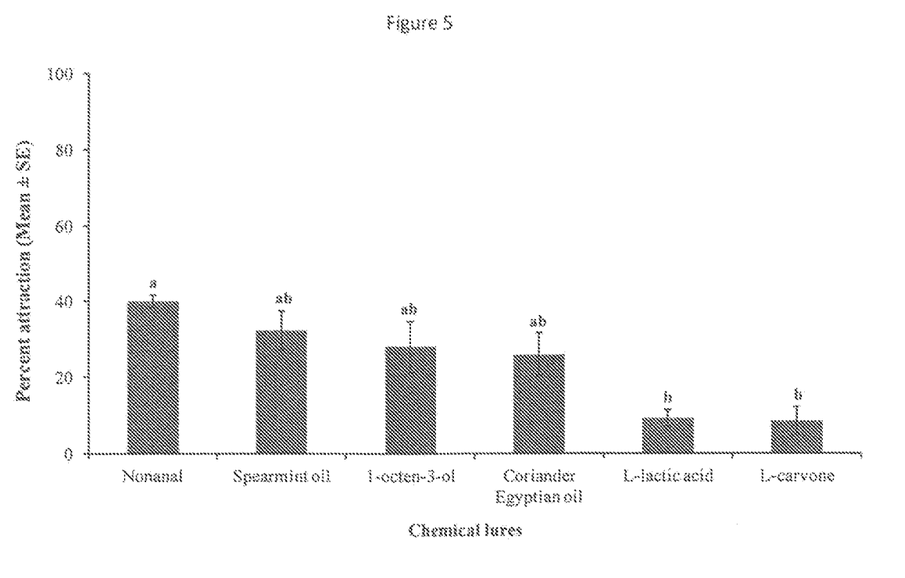
FIG. 5: Attraction of bed bugs to pitfall traps baited with chemical lures in two-choice bioassays. Bars with different letters are significantly different ($P<0.05$, Tukey's HSD test).
Figure 6:
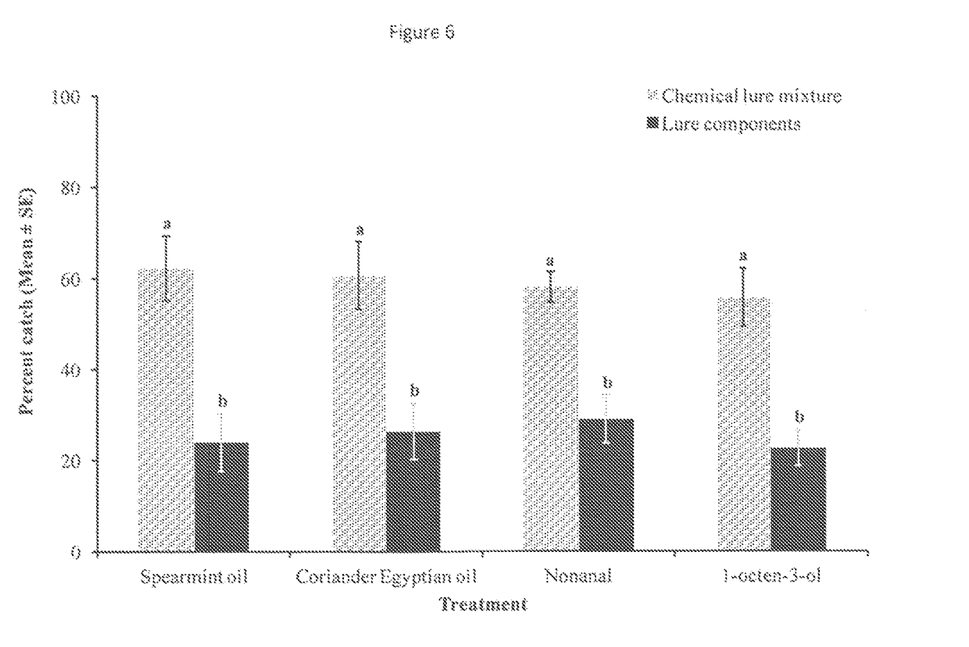
FIG. 6: Percent catch of bed bugs in pitfall traps baited with a chemical lure mixture and individual lure components. Bars with different letters are significantly different (P<0.05, paired t-test).
Figure 7:
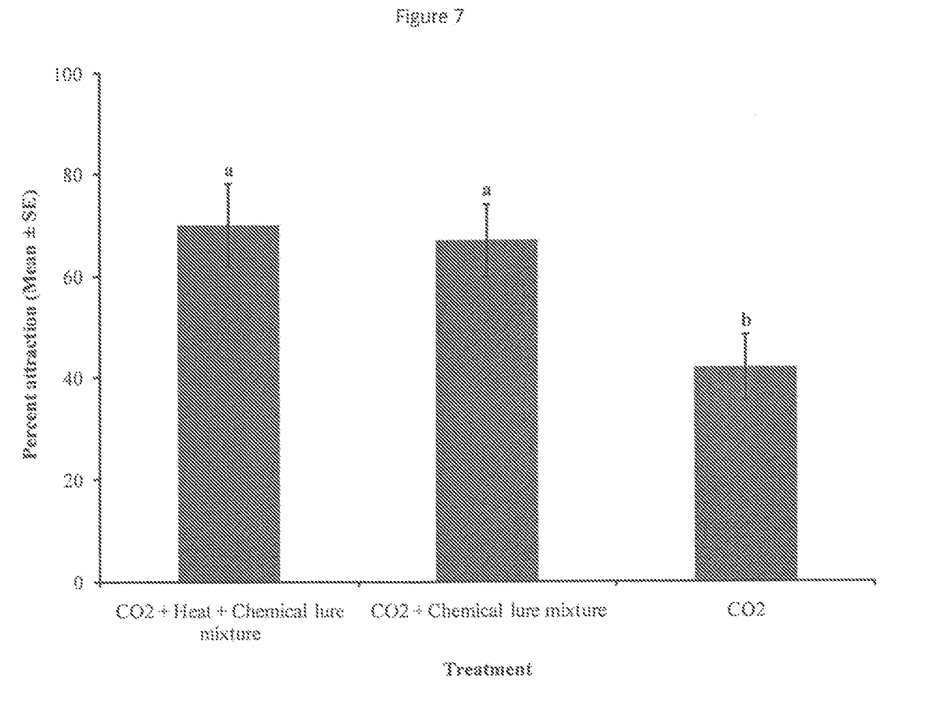
FIG. 7: Attraction of bed bugs to pitfall traps baited with 200 ml/min $CO_2$ alone or combinations of $CO_2$ and heat (4 mini hand warmers) and/or chemical lure mixture. Bars with different letters are significantly different (P<0.05, Tukey's HSD test).

Out of the twelve bed bug attractants evaluated in four-choice bioassays; nonanal, 1-octen-3-ol, spearmint oil, coriander Egyptian oil, L-lactic acid, and L-carvone baited traps caught significantly higher number of bugs than their corresponding controls (P<0.05) (Table 1). In two-choice bioassays, nonanal was significantly more attractive than L-lactic acid, and L-carvone ($\chi^2$=10, df=5, P=0.03, Kruskal-Wallis Tests) (FIG. 5). Spearmint oil, 1-octen-3-ol, and coriander Egyptian oil were not significantly different from nonanal (P>0.05). Further analysis in multiple comparison experiments showed that pitfall traps baited with nonanal, coriander Egyptian oil, 1-octen-3-ol and spearmint oil captured 34.0±4.6, 18.2±3.9, 17.0±1.8, and 16.4±4.0% of bed bugs, respectively. Nonanal was approximately 2-fold more attractive than spearmint oil, 1-octen-3-ol, or coriander Egyptian oil ($\chi^2$=6.2, df=3, P=0.01, Kruskal-Wallis Tests). The mean percentages of bed bugs in traps baited with a chemical lure mixture comprising nonanal, spearmint oil, 1-octen-3-ol, and coriander Egyptian oil, and their corresponding unbaited control traps were 49.5±5.9, and 20.2±4.1%, respectively. The chemical lure mixture increased trap catches by 2.5-fold than the unbaited control (P<0.05). This chemical lure mixture was approximately 2-fold more attractive than any of the four individual lure components (P<0.05) (FIG. 6). Traps with a combination of either chemical lure mixture+$CO_2$, or chemical lure mixture+$CO_2$+heat captured significantly more bed bugs compared to the trap baited with $CO_2$ only ($\chi^2$=4.8, df=2, P=0.02). However, there were no significant differences in percent attraction between traps baited with chemical lure mixture+$CO_2$ and traps baited with chemical lure mixture+$CO_2$+heat (P<0.05). When $CO_2$ was present, adding chemical lure increased percent attraction by 1.6-fold (FIG. 7).

Discussion

Our experiments demonstrated the attractiveness of four chemical lures to bed bugs: nonanal, 1-octen-3-ol, spearmint oil, and coriander Egyptian oil. Among these, nonanal was the most attractive chemical lure. Nonanal has been reported to play a major role in the chemical ecology of triatomine bugs [21], *Aedes aegypti* L. [22], and *Anopheles gambiae* Giles [23]. Nonanal was also the major compound found in odorant profiles of humans, chicken and pigeon, and elicited strong response in antenna of southern house mosquito, *Culex pipiens quinquefasciatus* Say [24]. Traps baited with nonanal and $CO_2$ caught higher number of southern house mosquitoes than traps baited with $CO_2$ alone [24]. 1-octen-3-ol has been reported to attract different blood sucking insects including bed bugs [10, 11], *Triatoma infestans* Klug [25], *Glossina* spp. [26] and *Aedes* and *Culex* spp. mosquitoes [27, 28]. Spearmint oil and coriander Egyptian oil are plant derived. L-carvone is the major component (51%) present in spearmint oil [29]. Its enantiomer, D-carvone has been patented as an attractant for Culicidae mosquitoes [30]. Coriander Egyptian oil has the aroma similar to odors emitted by bed bugs [31].

$CO_2$ was very attractive to bed bugs regardless of the $CO_2$ release rates being used when tested in door arenas, indicating that 200 ml/min rate is sufficient for attracting bed bugs in a room that is 2 m in length. Marx [9] and Anderson [10] reported that bed bugs can locate a host that is 150 cm and 86 cm away. The 200 ml/min rate seems to exceed the bed bugs response threshold and any higher concentrations above that were not helpful in enhancing their responses in door arenas. Under field conditions where a typical room is much larger, the minimum effective $CO_2$ release rate might be larger. Moreover, bed bug hunger levels, air current, and presence of a human host will affect the bed bugs response to $CO_2$ and trap catches.

Adding a mixture of four bed bug attractants (nonanal, 1-octen-3-ol, spearmint oil, and coriander Egyptian oil) increased bed bug trap catches by 1.6-fold when $CO_2$ was present, indicating the additive effect of chemical lures and $CO_2$ on bed bug host searching behavior. Similarly, Allan [7] found greater attraction in *Culex* spp. by the combined use of feathers and $CO_2$ than by using each component alone. Mixture of 1-octen-3-ol with $CO_2$ was reported to be more attractive than $CO_2$ alone in *Culex salinarius* [32, 33]. The *Amblyomma variegatum* F. were found to be more attractive to pheromone+$CO_2$ than $CO_2$ alone [34]. Host seeking in *A. variegatum* involves activation and a non-directional searching activity by $CO_2$; and a directional movement to pheromone and to other host emanating odors [34]. A closely related hematophagous hemipteran, *Triatoma infestans* Klug, also uses a combination of host cues to locate a host.

$CO_2$ served as a long range cues in its non-oriented searching behavior and when bug arrives in close proximity of its host, then radiant heat and chemical odors from the host oriented them to the exact host location [35]. It is possible that bed bugs' host searching behavior follows a similar sequence as *T. infestans* or *A. variegatum*.

The presence of either two or four hand warmers (or a 0.8-1.6° C. difference in temperature between the lip of the trap and the ambient air) attracted bed bugs from a distance of 25 cm. Nevertheless, the role of heat became insignificant when used in combination with $CO_2$ in wooden door arenas. A gradient of $CO_2$ concentration in the environment obscured the effect of heat. In contrast, the role of chemical lure mixture was significant even when $CO_2$ was present.

Wang [36] showed the effectiveness of pitfall traps baited with $CO_2$ alone for detecting very low level bed bug populations. But none of the bed bug monitors provide 100% assurance of the presence/absence of bed bugs in field environments. Results from this study suggest adding an inexpensive chemical lure to a trap may significantly improve the trap efficacy, and provide more accurate monitoring of bed bug infestations. Wang [36] suggested that an effective monitor can be used in unoccupied infested rooms to trap the hungry bed bugs, and for reducing the probability of bed bugs dispersing into adjacent uninfested rooms. An effective monitoring/trapping system for bed bugs could also be combined with insecticides or other killing agents to help control bed bug infestations.

It is noteworthy to mention that the bed bug strain, hunger level, arena size, and test room conditions had significant impacts on the test results in our experiments. Even within a test arena, there could be a location effect. When testing the effect of chemical lures or heat alone, we used small plastic arenas and a room with still air. When testing $CO_2$ or combination of $CO_2$ and heat and/or chemical lure, we used door arenas in ventilated rooms, which mimic the field conditions. Field conditions are usually much more complex than laboratory environments. The presence of a human host, clutter, furniture, and various odors from food and household cleaning agents could significantly affect the performance of a bed bug monitor.

REFERENCES

[1] P. G. Guerenstein and C. R. Lazzari, "Host-seeking: how triatomines acquire and make use of information to find blood," *Acta Tropica*, vol. 110, pp. 148-158, 2009.

[2] R. A. I. Norval, C. E. Yunker, and J. F. Butler, "Field sampling of unfed adults of *Amblyomma hebraeum* Koch," *Experimental and Applied Acarology*, vol. 3, pp. 213-217, 1987.

[3] R. A. I. Norval, J. F. Butler, and C. E. Yunker, "Use of carbon dioxide and natural or synthetic aggregation-attachment pheromone of the bont tick, *A. hebraeum*, to attract and trap unfed adults in the field," *Experimental and Applied Acarology*, vol. 7, pp. 171-180, 1989.

[4] J. Colvin and G. Gibson, "Host-seeking behavior and management of Tsetse," *Annual Review of Entomology*, vol. 37, pp. 21-40, 1992.

[5] S. N. Puri, M. J. Mendki, D. Sukumaran, K. Ganesan, S. Prakash, and K. Sekhar, "Electroantennogram and behavioral responses of *Culex quinquefasciatus* (Diptera: Culicidae) females to chemicals found in human skin emanations," *Journal of Medical Entomology*, vol. 43, pp. 207-213, 2006.

[6] W. Takken and B. G. J. Knols, "Odor-mediated behavior of Afrotropical malaria mosquitoes," *Annual Review of Entomology*, vol. 44, pp. 131-157, 1999.

[7] S. A. Allan, U. R. Bernier, and D. L. Kline, "Laboratory evaluation of avian odors for mosquito (Diptera: Culicidae) attraction," *Journal of Medical Entomology*, vol. 43, pp. 225-231, 2006.

[8] C. B. Russell and F. F. Hunter, "Attraction of *Culex pipiens*/restuans (Diptera: Culicidae) mosquitoes to bird uropygial gland odors at two elevations in the Niagara Region of Ontario," *Journal of Medical Entomology*, vol. 42, pp. 301-305, 2005.

[9] R. Marx, "Über die Wirtsfindung und die Bedeutung des artspezifischen Duftstoffes bei *Cimex lectularius* Linné. *Zeitschrift für Parasitenkunde,"* vol. 17, pp. 41-73, 1955.

[10] J. F. Anderson, F. J. Ferrandino, S. McKnight, J. Nolen, and J. Miller, "A carbon dioxide, heat and chemical lure trap for the bedbug, *Cimex lectularius*," *Journal of Medical and Veterinary Entomology*, vol. 23, pp. 99-105, 2009.

[11] C. L. Wang, T. Gibb, G. W. Bennett, and S. McKnight, "Bed bug (Heteroptera: Cimicidae) attraction to pitfall traps baited with carbon dioxide, heat, and chemical lure," *Journal of Economic Entomology*, vol. 102, pp. 1580-1585, 2009.

[12] E. Rivnay, "Studies in tropisms of the bed bug, *Cimex lectularius* L.," *Parasitology* Vol. 24, pp. 121-136, 1932.

[13] A. E. Aboul-Nasr and M. A. S. Erakey, "Behaviour and sensory physiology of the bed bug, *Cimex lectularius* L., to some environmental factors: chemoreception (Hemiptera: Cimicidae)," *Bulletin of the Entomological Society of Egypte,* vol. 52, pp. 353-362, 1968.

[14] B. Wertheim, E. J. A. van Baalen, M. Dicke, and L. E. M. Vet., "Pheromone-mediated aggregation in nonsocial arthropods: an evolutionary ecological perspective," *Annual Review of Entomology*, vol. 50, pp. 321-346, 2005.

[15] E. Siljander, D. Penman, H. Harlan, and G. Gries, "Evidence for male- and juvenile-specific contact pheromones of the common bed bug *Cimex lectularius*," *Entomologia Experimentalis et Applicata*, vol. 125, pp. 215-219, 2007.

[16] E. Siljander, R. Gries, G. Khaskin, and G. Gries, "Identification of the airborne aggregation pheromone of the common bed bug, *Cimex lectularius*," *Journal of chemical Ecology*, vol. 34, pp. 708-718, 2008.

[17] C. Boase, "Bedbugs-back from the brink," *Pesticide Outlook*, vol. 12, pp. 159-162, 2001.

[18] A. R. Leff and P. T. Schumacker, "*Respiratory Physiology Basics and Applications,"* pp. 52-54, W.B. Saunders Co., Philadelphia, Pa., 1993.

[19] T. Suzuki and R. Sugawara, "Isolation of an aggregation pheromone from the flour beetles, *Triboliurn castaneum* and *T. confusum* (Coleoptera: Tenebrionidae)," *Journal of Applied Entomology and Zoology*, vol. 14, pp. 228-230, 1979.

[20] JMP, Version 8, SAS Institute Inc., Cary, N.C., 2009.

[21] P. G. Guerenstein and P. M. Guerin, "Olfactory and behavioural responses of the blood-sucking bug *Triatoma infestans* to odours of vertebrate hosts," *The Journal of Experimental Biology*, vol. 204, pp. 585-597, 2001.

[22] M. Ghaninia, M. Larsson, B. S. Hansson, and R. Ignell, "Natural odor ligands for olfactory receptor neurons of the female mosquito *Aedes aegypti*: Use of gas chromatography linked single sensillum recordings," *The Journal of Experimental Biology*, vol. 211, pp. 3020-3027, 2008.

[23] J. Meijerink, M. A. H. Braks, and J. J. A. Van Loon, "Olfactory receptors on the antennae of the malaria mosquito *Anopheles gambiae* are sensitive to ammonia and other sweat borne components," *Journal of Insect Physiology*, vol. 47, pp. 455-464, 2001.
[24] Z. Syed and W. S. Leal, "Acute olfactory response of *Culex* mosquitoes to a human- and bird-derived attractant," *Proceedings of the National Academy of Sciences of the United States of America*, vol. 106, pp. 18803-18808, 2009.
[25] R. B. Barrozo and C. R. Lazzari, "The response of the blood-sucking bug *Triatoma infestans* to carbon dioxide and other host odours," *Chemical Senses*, vol. 29, pp. 319-329, 2004.
[26] G. A. Vale and D. R. Hall, "The role of 1-octen-3-ol, acetone and carbon dioxide in the attraction of tsetse flies, *Glossina* spp. (Diptera: Glossinidae), to ox odor," *Bulletin of Entomological Research*, vol. 75, pp. 209-217, 1985.
[27] P. H. Van Essen, J. A. Kemme, S. A. Ritchie, and B. H. Kay, "Differential responses of *Aedes* and *Culex* mosquitoes to octenol or light in combination with carbon dioxide in Queensland, Australia," *Medical and Veterinary Entomology*, vol. 8, pp. 63-67, 1994.
[28] D. L. Kline, "Traps and trapping techniques for adult mosquito control," *Journal of the American Mosquito Control Association*, vol. 22, pp. 490-496, 2006.
[29] J. L. Theodore, G. G. Dante, H. Jean, R. M. Thomas, and R. Teranishi, "Chemical and sensory data supporting the difference between the odors of the enantiomeric carvones", *Journal of Agricultural and Food Chemistry*, vol. 19, pp. 785, 1971.
[30] R. A. Wilson, J. F. Butler, D. Withycombe, B. D. Mookherjee, I. Katz, and K. R. Schrankel, "Use of d-carvone as mosquito attractant," U.S. Pat. No. 4,970,068, 1992.
[31] Wikipedia, "Bed bugs," September 2011, http://en.wikipedia.org/wiki/Bed_bug.
[32] D. L. Kline, "Olfactory attractants for mosquito surveillance and control: 1-octen-3-ol," *Journal of the American Mosquito Control Association*, vol. 10, pp. 280-287, 1994.
[33] L. M. Rueda, B. A. Harrison, J. S. Brown, P. B. Whitt, R. L Harrison, and R. C. Gardner, "Evaluation of 1-octen-3-ol, carbon dioxide, and light as attractants for mosquitoes associated with two distinct habitats in North Carolina," *Journal of the American Mosquito Control Association*, vol. 17, pp. 61-66, 2001.
[34] R. O. Maranga, A. Hassanali, G. P. Kaaya, and J. M. Mueke, "Attraction of *Amblyomma variegatum* (ticks) to the attraction-aggregation-attachment pheromone with or without carbon dioxide," *Experimental and Applied Acarology*, vol. 29, pp. 121-130, 2003.
[35] R. Barrozo and C. Lazzari, "Orientation response of haematophagous bugs to $CO_2$: the effect of the temporal structure of the stimulus," *Journal of Comparative Physiology A: Neuroethology, Sensory, Neural, and Behavioral Physiology*, vol. 192, pp. 827-831, 2006.
[36] C. Wang, W. T. Tsai, R. Cooper, and J. White, "Effectiveness of bed bug monitors for detecting and trapping bed bugs in apartments," *Journal of Economic Entomology*, vol. 104, pp. 274-278, 2011.

EXAMPLE II

Field Evaluation of the Inventive Chemical Lure Mixture for Attracting Bed Bugs

In the present example, we determined whether an experimental lure mixture enhances bed bug trap catches under field conditions.

Material and Methods

Study site. The study was conducted in two apartments located in Newark, N.J. Each apartment had a bedroom, living room, a kitchen, and a bathroom. Total area of each apartment was 600 ft$^2$. Each apartment was occupied by one elderly person. Both apartments had high numbers of bed bugs. Apartment "A" was more severely infested than apartment "B" based on our visual inspections.

Pairs of Climbup Insect Interceptors (Susan McKnight, Inc., Memphis, Tenn.), referred to hereafter as "traps", were installed on floors adjacent to walls, corners, and under the beds. Within each pair, a centrifuge tube containing 100 μl lure mixture was placed at the center of one trap. The vial lid had a 2 mm diameter opening for release of lure into the air. The other trap did not contain any lure. The distances between the baited and un-baited traps were approximately 30 cm. Eleven and six pairs were placed in apartment "A" and "B", respectively.

The numbers of bed bugs caught in the traps were recorded after 2 days (referred as "period 1"). Then the baited and un-baited trap positions were switched, and the bed bug numbers inside the traps were recorded after 6 days (referred as Period 2).

Data Analysis.

Those trap pairs with a total of less than 10 bed bugs were not included in the analysis. A paired t-test (P=0.05) was used to compare the bed bug counts in baited and un-baited traps for each sampling date.

Results

Figure 8:
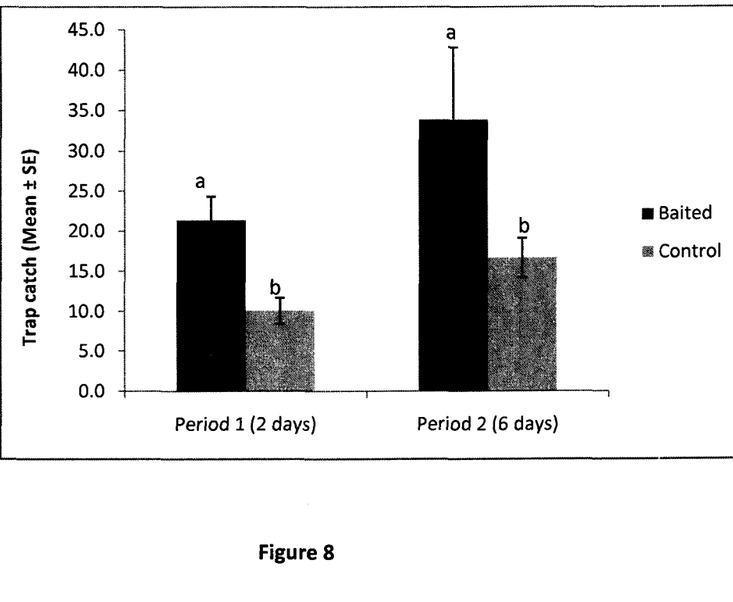
FIG. 8: Effect of chemical lure mixture on trap catches. Within the same sampling period, bars with different letters are significantly different (P<0.05, paired t-test).

During Period 1, baited traps caught an average of 2.8-fold more bed bugs than the un-baited traps. During Period 2, the baited traps caught an average of 2.1-fold more bed bugs than the un-baited traps (FIG. 8). The baited traps caught significantly more bed bugs than the un-baited traps both in Period 1 (t=2.26; df=16; P<0.04) and in Period 2 (t=3.86; df=15; P<0.002).

Discussion

These results corroborated our laboratory findings that the chemical lure mixture is attractive to bed bugs and can significantly enhance the effectiveness of a bed bug monitor. The lure may also be used in conjunction with other types of trapping devices to monitor or control bed bugs by simply placing the lure on top or inside the trapping devices. Previous studies have shown that using bed bug monitors is a much more reliable and less time consuming than visual inspections for identifying low level bed bug infestations (Wang et al. 2009, 2011). We expect that by incorporating an effective lure into the monitors, consumers and pest management professionals will be able to detect bed bugs more easily and save cost in bed bug monitoring and management.

EXAMPLE III

Modifications and Improvements in the Inventive Chemical Lure Mixture

In this example, we assess modifications of the inventive chemical lures of the invention for their attractiveness to bed bugs.

Material and Methods

Bed bugs were collected from an infested apartment in Newark, N.J. They were maintained in plastic containers with folded paper as harborages at 26±1° C., 40±10% relative humidity, a 12:12 hour (L:D) photoperiod. They were fed weekly on rabbit blood using a Hemotek membrane-feeding system (Discovery Workshops, Accrington, UK). Bugs were not fed for 2 weeks prior to bioassays. Only males and large bed bug nymphs were used in this study.

Figure 9A:
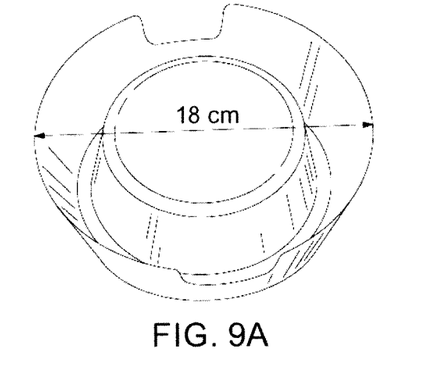
FIG. 9: Experimental set up for determining bed bug attraction to chemical lures. A) pitfall traps were used in all bioassays; b) plastic tray arena with a baited and unbaited trap.

Pitfall traps were used to evaluate the attractiveness of various lures. The pitfall trap was an inverted plastic dog bowl (600 ml volume, 18 cm diameter, 6.4 cm deep and 1 mm thickness) (IKEA, Baltimore, Md., USA) (FIG. 9a). The outer wall of the trap was covered with a layer of paper surgical tape (Caring International, Mundelein, Ill., USA), which was dyed black with Fiebing's Leather Dye (Tandy Leather Factory, Fort Worth, Tex., USA) (FIG. 9a). The inside surfaces of both trap types were coated with a light layer of fluoropolymer resin (DuPont Polymers, Wilmington, Del., USA) to prevent trapped bed bugs from escaping.

Figure 9B:
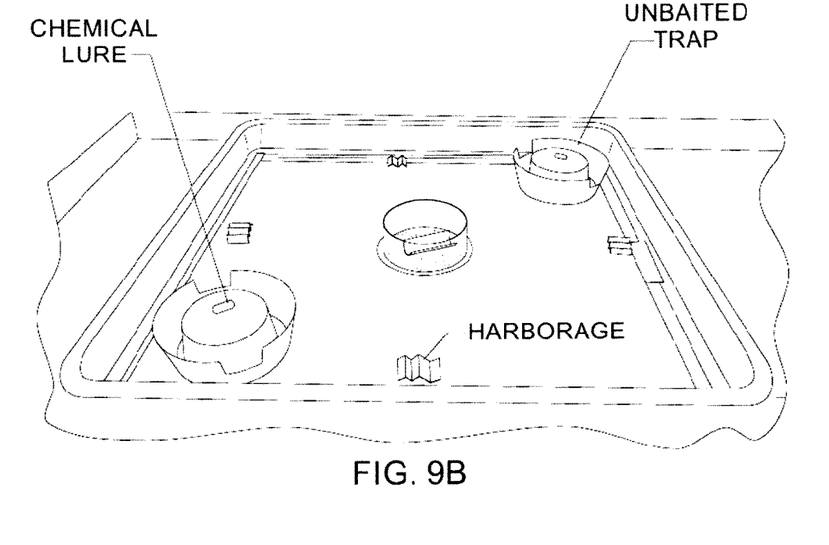

Plastic tray arenas (80 by 75 by 5 cm) (length by width by height) with bottom lined with brown paper were used (FIG. 9b). A layer of fluoropolymer resin was applied to inner walls of the arenas to prevent the bugs from escaping. A filter paper (15 cm diameter) was placed on the floor in the center of each arena, and then a plastic ring (13.3 cm diameter and 6.4 cm height) was placed on the filter paper for confining the bed bugs. A piece of folded cardboard and folded fabric was placed on the filter paper to provide harborages for bed bugs. Four additional paper harborages measuring 5.1 cm long and 3.3 cm wide were placed along the edges of the floor of each tray arena. Four or six arenas were placed simultaneously in a non-ventilated, closed room measuring 4 m long and 2.3 m wide at 24-25° C. A 12:12 hour (L:D) cycle was maintained in the room that was used for bioassays.

Experiment 1. Attractiveness of L-Lactic Acid in the Inventive Chemical Lure Mixture A 5-chemical lure mixture (Nonanal, 1-octen-3-ol, L-lactic acid, spearmint oil, and coriander Egyptian oil) was compared with a 4-chemical lure mixture (Nonanal, 1-octen-3-ol, spearmint oil, and coriander Egyptian oil). Ten microliter of each chemical was dispensed onto cotton within a 0.7 ml micro centrifuge tube. The lid of each tube had a 2 mm diameter opening to allow for slow release of the chemical. Each plastic tray arena had two traps: one trap was used as an unbaited control and the other trap received a chemical lure mixture. Two arenas were baited with a 5-chemical lure mixture and the other two arenas were baited with a 4-chemical lure mixture. Bed bug numbers in each trap were recorded after 8 h. The experiment was repeated the next day. The locations of a 5-chemical lure and 4-chemical lure mixture baited traps were switched on the second day.

Experiment 2. Attractiveness of Spearmint Oil and Coriander Egyptian Oil in the Inventive Chemical Lure Mixture A 5-chemical lure mixture (Nonanal, 1-octen-3-ol, L-lactic acid, spearmint oil, and coriander Egyptian oil) was compared with 3-chemical lure mixture (Nonanal, 1-octen-3-ol, and L-lactic acid). Three arenas were baited with a 5-chemical lure mixture and the other three arenas were baited with a 3-chemical lure mixture. The experiment was repeated the next day. The locations of the 5-chemical and 3-chemical lure mixture baited traps were switched on the second day. Other procedures were similar as Experiment 1.

Experiment 3. Attractiveness of Coriander Egyptian Oil in the Inventive Chemical Lure Mixture A 5-chemical lure mixture (Nonanal, 1-octen-3-ol, L-lactic acid, spearmint oil, and coriander Egyptian oil) was compared with 4-chemical lure mixture (Nonanal, 1-octen-3-ol, L-lactic acid, and spearmint oil). Other procedures were similar as in Experiment 1.

Mean percent attraction was calculated as: Percent attraction=$100\times(T-C)/(T+C)$, where "T" is the number of bed bugs in the baited pitfall trap and "C" is the number of bed bugs in the non-baited pitfall trap. The mean percent attractions were subject to Analysis of variance (ANOVA) to compare among treatments.

Results

The 5-chemical lure containing L-lactic acid was more attractive than the 4-chemical lure without L-lactic acid (P=0.03). The mean percentages of bed bugs trapped in 5-chemical and 4-chemical lure mixture were 34.4±2.8 and 25.3±1.8%, respectively. Significantly higher percentages of bed bugs were found in traps baited with 5-chemical lure mixture (45.83±4.3%) than those baited with 3-chemical lure mixture (27.04±6.6%) that did not contain spearmint oil and coriander Egyptian oil (P=0.04). The 5-chemical lure mixture was equally effective as the 4-chemical lure mixture that lacked coriander Egyptian oil (P=0.52). The 5-chemical lure and the 4-chemical lure without coriander Egyptian oil trapped 40.5±7.9% and 34.4±4.7% bed bugs, respectively.

Discussion

Results show L-lactic acid was important component of the lure mixture. Coriander Egyptian oil did not increase the effectiveness of the lure mixture when other 4 components were present. The nonanal, 1-octen-3-ol, L-lactic acid, and spearmint oil are the essential components and coriander Egyptian oil can be excluded from the chemical lure mixture.

EXAMPLE IV

Comparison of a Commercial Bed Bug Lure and the Chemical Lure Mixture of the Invention Using a Commercial Bed Bug Monitor In the present example, we compare the attractiveness of a commercial bed bug lure and the chemical lure mixture of the invention to bed bugs using a commercial bed bug monitor.

Material and Methods

Bed bugs were collected from an infested apartment in New Brunswick, N.J. They were maintained in plastic containers (4.7 cm height and 5 cm diameter) with folded paper as harborages at 26±1° C., 40±10% relative humidity, a 12:12-hour (L:D) photoperiod, and were deprived of food for the entire duration of the study. Bugs were very well fed at the time of collection. Only males and large bed bug nymphs were used in this study. All bioassays were conducted within 3 weeks after bed bugs were collected.

Four plastic tray arenas (80 by 75 by 5 cm) (length by width by height) with bottom lined with brown paper were used simultaneously in a non-ventilated, closed room measuring 4 m long and 2.3 m wide at 24-25° C. A 12:12-hour (L:D) cycle was maintained in the bioassay room. All the arenas were at least 1.5 m away from each other. A mock bed comprising the foam mattress and a bed sheet was placed in each arena. Four bed bug exposed paper harborages containing bed bug feces and cast skins were placed on the floor of arena. Eighty bed bug nymphs and adult males were released into the center of mock bed and confined with a plastic ring for 1 hour (FIG. 10). Plastic ring was then removed and the bugs were allowed to disperse uniformly and acclimated in the arena for approximately 15 hours prior to the start of the experiment. A commercial bed bug monitor was used to test both lures. The two monitors were placed at opposite ends of the mock bed (FIG. 10, the monitors were not shown here).

The lures to be tested were housed in plastic tubes. Two tubes were placed inside each bed bug monitor. Each tube containing the commercial bed bug lure had a 0.5 mm hole on the seal. The tubes with Rutgers lure had a 1.5 mm or 0.5 mm diameter hole. Two tubes each with 200 µl Rutgers chemical lure mixture were placed inside a monitor. Two tubes with a total of 400 ul commercial lure were placed in each monitor. Each arena had an unbaited monitor and a monitor baited with one of the two lures.

At 1 hour after dark cycle, both the unbaited and baited monitors were placed in the arena. The numbers of bed bugs trapped in the monitors and those in the arenas were collected and counted after 30 hours with the aid of a red light. After counting, dead and moribund bugs were replaced with healthy bugs in each arena. All bugs were placed back to the center of mock bed, confined with plastic rings for 1 hour and then allowed to disperse for 15 hours before starting the next bioassay. The commercial lure was tested in four arenas on the first day. The Rutgers lure with 0.5 mm opening was tested in four arenas on the $3^{rd}$ day and on the $5^{th}$ day. A paired t-test was used for comparing percent trap catches between an unbaited and baited monitor.

Results

The lure tube containing the lure mixture described herein along with a 1.5 mm opening significantly increased the trap catches (P<0.05, paired t-test). The mean percentages of bed bugs in unbaited and Rutgers chemical lure mixture baited monitors were 22.0±4.0, and 33.6±6.0%, respectively. Rutgers lure increased the trap catch by an average 56%. The commercial bed bug lure with 0.5 mm opening on the tube did not significantly affect trap catch (P>0.05, paired t-test). The mean percentages of bed bugs in unbaited monitors and monitors baited with commercial bed bug lure were 24.8±6.9 and 33.8±5.2%, respectively. The inventive lure with a 0.5 mm opening did not significantly increase trap catches (P>0.05, paired t-test). The mean percentages of bed bugs in unbaited monitor and monitors baited with the inventive chemical lure mixture with 0.5 mm opening were 20.5±4.3, and 35.2±5.8%, respectively.

Discussion

When lure tubes had 0.5 mm openings on the seal, neither commercial bed bug lure nor Rutgers chemical lures could significantly increase the monitor efficacy. However, in three out of the four replicates, both lures increased trap catches. When the opening size was increased to 1.5 mm, Rutgers chemical lure mixture caught significantly higher number of bed bugs than the unbaited monitors after overnight.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A composition for luring *Cimex lectularius* or *Cimex hemipterus*, said composition consisting essentially of nonanal, octenol, spearmint oil, and coriander Egyptian oil in a suitable carrier.

2. A composition as claimed in claim 1, further consisting essentially of lactic acid.

3. A method for monitoring for the presence of bed bugs, selected from *Cimex lectularius* and *Cimex hemipterus*, using an intercepting device, which comprises an upstanding, exterior climbable surface that bed bugs can climb, and a pitfall trap disposed inwardly of the climbable exterior surface, wherein bed bugs are trapped as a result of being unable to climb out, the method comprising: installing in the intercepting device a lure composition consisting essentially of nonanal, octenol, spearmint oil, and coriander Egyptian oil in a suitable carrier and a source of $CO_2$ and optionally heat, and placing the intercepting device in an area to be monitored.

4. A composition for luring *Cimex lectularius* or *Cimex hemipterus*, said composition consisting essentially of nonanal, octenol, spearmint oil, and L-lactic acid in a suitable carrier.

5. A system for trapping *Cimex lectularius* or *Cimex hemipterus* comprising: an upstanding, exterior climbable surface that bed bugs can climb, and a pitfall trap positioned inwardly of the climbable exterior surface, wherein bed bugs are trapped as a result of being unable to climb out; an electrical or chemical means for maintaining a temperature of at least about normal body temperature; a source of carbon dioxide; and a lure composition consisting essentially of nonanal, octenol, spearmint oil, and L-lactic acid, in a suitable carrier.

6. A system for trapping *Cimex lectularius* or *Cimex hemipterus* as claimed in claim 5, wherein said lure composition consists essentially of nonanal, octenol, spearmint oil, coriander Egyptian oil and L-lactic acid in a suitable carrier.

7. The system of claim 5, wherein said source of carbon dioxide is effective to release carbon dioxide at a rate of 200 mL/min to 500 mL/min.

* * * * *